(12) United States Patent
Goralski et al.

(10) Patent No.: US 6,362,373 B1
(45) Date of Patent: Mar. 26, 2002

(54) CHIRAL AMINO ALCOHOLS AND PROCESS FOR PREPARATION OF SAME

(75) Inventors: Christian T. Goralski, Midland, MI (US); Bakthan Singaram, 206 Dickens Way, Santa Cruz, CA (US) 95064; William Chrisman, 654 Georgia Ave., Palo Alto, CA (US) 94306

(73) Assignees: The Dow Chemical Company, Midland, MI (US); Bakthan Singaram, Santa Cruz; William Chrisman, Palo Alto, both of CA (US)

( * ) Notice: Subject to any disclaimer, the term of this patent is extended or adjusted under 35 U.S.C. 154(b) by 0 days.

(21) Appl. No.: 09/661,421

(22) Filed: Sep. 13, 2000

(51) Int. Cl.[7] .................. C07C 209/22; C07C 211/34; C07C 211/35

(52) U.S. Cl. ............. 564/392; 564/445; 564/457; 540/609; 544/59; 544/173; 544/389; 544/398; 546/139; 546/227; 546/240; 548/341.1; 548/575

(58) Field of Search .................. 540/609; 544/59, 544/173, 389, 398; 546/139, 227, 240; 548/341.1, 575; 564/392, 445, 457

(56) References Cited

U.S. PATENT DOCUMENTS 3,960,539 A * 6/1976 Newhall ...................... 71/76
4,040,813 A * 8/1977 Newhall ...................... 71/121

OTHER PUBLICATIONS

Database CAPLUS on STN, Acc. No. 1978:191084 Kozhin et al., 'Products of the aminolysis of limonene 1,2–monoxide.' Zh. Obshch. Khim. (1978), 48(1), pp. 203–217 (abstract).*

Patrick, R.; Newhall, W.F., J. Agr. Food Chem. 1960, 8, p. 397.*
Kuczynski, H.; Zabza, A., Bull. Acad. Polon. Sci., Ser. Sci. Chim. 1961, 9, p. 551.*
Kuczynski, H.; Zabza, A., Roczniki Chem. 1963, 37, p. 773.*
Newhall, W.F.; J. Org. Chem. 1964, 29, p. 185.*
Wylde, R.; Teulon, J.M., Bull. Soc. chim. Fr. 1970, 2, p. 758.*
Kozhin, S.A.; Zaitsev, V.V.; Ionin, B.I., Zh. Obshch. Khim. 1978, 48, p. 203.*
Baker, R.; Borges, M.; Cooke, N.G.; Herbert, R.H., J. Chem. Soc., Chem. Commun. 1987, p. 414.*
Pavia, A. A., et al., "Hydrogénation en phase liquide sur Pd/C de dérivés mono et disubstitués du limonène.", Bulletin De La Société Chimique De France 1981 No. 1–2., Part 2, 24–27.

* cited by examiner

*Primary Examiner*—Brian J. Davis

(57) ABSTRACT

The disclosed invention comprises a compound having the formula:

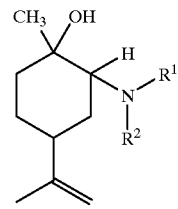

in which $R^1$ and $R^2$ independently represent a hydrogen or an alkyl group of 4 carbon atoms or greater. Further disclosed is a process for the preparation of the disclosed chiral amino alcohols from a starting amine compound and a limonene oxide.

7 Claims, No Drawings

CHIRAL AMINO ALCOHOLS AND PROCESS FOR PREPARATION OF SAME

BACKGROUND OF THE INVENTION

1. Field of the Invention

The invention relates to chiral amino alcohols and a process for their preparation. More particularly, the invention relates to 2-(dialkylamino)-1-methyl-4-(1-methylethenyl)cyclohexanols and 2-(alkylamino)-1-methyl-4-(1-methylethenyl)cyclohexanols and the preparation of the aforementioned chiral amino alcohols from a starting amine compound and a limonene oxide.

2. Description of the Prior Art

The following references are cited as prior art:
1. Patrick, R.; Newhall, W. F. *J. Agr. Food Chem.* 1960, 8, 397.
2. Kuczynski, H.; Zabza, A. *Roczniki Chem.* 1961, 35, 1621.
3. Kuczynski, H.; Zabza, A. *Bull. Acad. Polon. Sci., Ser. Sci. Chim.* 1961, 9, 551.
4. Kuczynski, H.; Zabza, A. *Roczniki Chem.* 1963, 37, 773.
5. Newhall, W. F. *J. Org. Chem.* 1964, 29, 185.
6. Wylde, R.; Teulon, J. M. *Bull Soc. Chim. Fr.* 1970, 2, 758.
7. Kozhin, S. A.; Zaitsev, V. V.; Ionin, B. I. *Zh. Obshch. Khim.* 1978, 48, 203.
8. Pavia, A. A.; Geneste, P.; Olive, J. L. *Bull. Soc. Chim. Fr.* 1981, Part 2, 24.
9. Baker, R.; Borges, M.; Cooke, N. G.; Herbert, R. H. *J. Chem. Soc., Chem. Commun.* 1987, 414.
10. The following two structures have assigned CAS numbers, but no references were listed: p-Meth-8-en-1-ol, 2-piperidino-[92792-99-9]; Cyclohexanol, 1-methyl-4-(1-methylethenyl)-2-(1-piperidinyl)-, (1α,2β,4α)-[6756-83-8]

Newhall, U.S. Pat. No. 3,960,539
Newhall, U.S. Pat. No. 4,040,813

Reference 1 teaches the use of 2-dimethylamino-1-methyl-4-(1-methylethenyl)cyclohexanol (no stereochemistry indicated) as a plant fungicide.

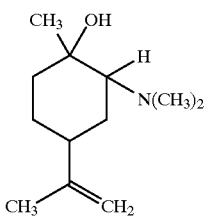

Reference 3 teaches the preparation of 2-dimethylamino-1-methyl-4-(1-methylethenyl)cyclohexanol from limonene oxide (there is some question about the stereochemistry presented in this paper—confusion exists in the literature as to what constitutes the cis and trans isomers of limonene oxide). This reference also reports the N-oxide of this amino alcohol.

Reference 4 also teaches the preparation of 3-dimethylamino-1-methyl-4-(1-methylethenyl) cyclohexanol from limonene oxide. This reference also teaches the preparation of the N-oxide of the dimethylamino compound.

Reference 5 teaches the reaction of limonene oxide with ammonia methylamine, and dimethylamine to give the corresponding amino alcohols. This reference also teaches the preparation of the N-oxide of the dimethylamino compound.

Reference 6 also teaches the reaction of dimethylamine with limonene oxide to give the corresponding amino alcohol.

Reference 7 teaches the reaction of limonene oxide with ammonia, methylamine, ethylamine, diethylamine, n-propylamine, isopropylamine, and benzylamine to give the corresponding amino alcohols and their salts.

Reference 8 teaches the reaction of limonene oxide with dimethylamine to give the corresponding amino alcohol.

Reference 9 teaches the reaction of (R)-(+)-limonene oxide and (S)-(−)-limonene oxide with dimethylamine to give the corresponding amino alcohols.

U.S. Pat. Nos. 3,960,539 and 4,040,813 describe the preparation of compounds of the general formula

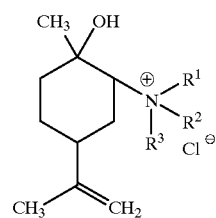

and their use as plant growth regulators, nematocides, and fungicides.

SUMMARY OF THE INVENTION

The invention comprises a compound having the formula:

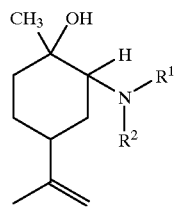

in which $R^1$ and $R^2$ independently represent hydrogen or an alkyl group of 4 carbon atoms or greater. Further claimed is a process for the preparation of the disclosed chiral amino alcohols from a starting amine compound and a limonene oxide.

DETAILED DESCRIPTION OF THE PREFERRED EMBODIMENTS

The invention comprises a compound having the formula:

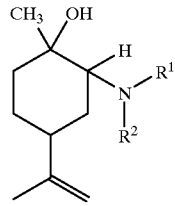

in which $R^1$ and $R^2$ independently represent a hydrogen or an alkyl group of 4 carbon atoms or greater, or in which $R^1$ and $R^2$ together form a carbocyclic ring containing five or more carbon atoms an which also may optionally contain a heteroatom selected from the group consisting of nitrogen, oxygen, or sulfur.

If $R^1$ and $R^2$ form a carbocyclic ring and n=1 or greater, then the following structure is created:

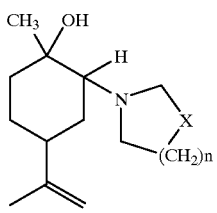

in which X=NH, NCOOR (with R= to an alkyl group of from 1 to 6 carbon atoms), NCOR (with R= to an alkyl group of from 1 to 6 carbon atoms), NR (with R= to an alkyl group of from 1 to 6 carbon atoms, a benzyl or substituted benzyl group, or a phenyl or substituted phenyl group, or CHR (with R= to an alkyl group of from 1 to 6 carbon atoms, a benzyl or substituted benzyl group, or a phenyl or substituted phenyl group, or CO$_2$H). The carbocyclic ring may optionally be fused to an aromatic ring to give compounds of the formula:

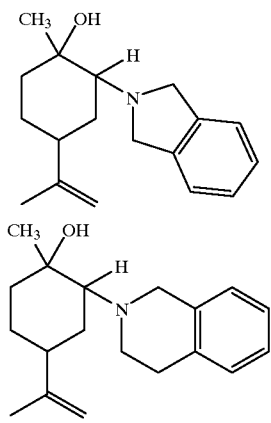

In all cases, the stereochemistry of the compounds may be (1S,2S,4R) or (1R,2R,4S).

The invention also comprises compounds of the general formula:

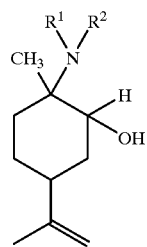

In which NR$^1$R$^2$ represents all of the amine combinations cited above.

The invention further comprises a process for preparing a chiral amino alcohol comprising the steps of providing an amine starting compound and a limonene oxide, refluxing the amine starting compound with the limonene oxide to form a chiral amino alcohol, removing excess amine and limonene oxide starting materials by distillation under reduced pressure of less than 10 Torr, forming the oxalate salt of the desired chiral amine by reaction of the crude product with oxalic acid in either methanol or acetone (or a mixture thereof), neutralizing the oxalate salt with aqueous potassium hydroxide, and purifying the desired amino alcohol by distillation or recrystallization.

In a preferred embodiment of the invention, the amine starting compound is selected from the group consisting of an alkyl amine with an alkyl group containing five or more carbon atoms, a dialkylamine containing alkyl groups containing five or more carbon atoms, a secondary amine in which the nitrogen is contained in a ring containing four or more carbon atoms (such amines include pyrrolidine, piperidine, hexamethyleneimine) and optionally may also contain a heteroatom consisting of the group including nitrogen, oxygen, and sulfur (such amines include morpholine, 4-methylpiperazine, 4-ethylpiperazine, ethyl 1-piperazinecarboxylate, and thiomorpholine). In addition, the amine may also contain a chiral center (such amines include (R)-alpha-methylbenzylamine, (S)-alpha-methylbenzylamine, (R)-1-cyclohexylethylamine, and (S)-1-cyclohexylethamine. The limonene oxide compound is preferably selected from the group consisting of (R)-(+)-limonene oxide or (S)-(–)-limonene oxide. As stated above, the amine starting compound is refluxed with the limonene oxide compound in the presence of water as a catalyst to form a chiral amino alcohol. The excess amine and limonene oxide are then distilled away at reduced pressure to give the crude amino alcohol. The crude amino alcohol is then treated with a solution of oxalic acid in either methanol or acetone (or a mixture thereof) to form the oxalic acid salt. The oxalic acid salt is isolated and may be further purified by recrystallization. The oxalate salt is neutralized with aqueous potassium hydroxide to give the desired amino alcohol. The amino alcohol may be purified by distillation or recrystallization as required. Optionally, after the reflux period is complete the reaction mixture is cooled to room temperature. The cooled reaction mixture is then dissolved in diethyl ether and the amino alcohol extracted into aqueous hydrochloric acid. The hydrochloric acid solution is then extracted with several of diethyl ether to remove any remaining limonene oxide. The amine is then converted to the free base form by neutralization of the aqueous hydrochloride solution with either sodium or potassium hydroxide. The amino alcohol is then extracted into diethyl ether and isolated by removal of the diethyl ether in vacuo (rotary evaporator). The amino alcohol is then purified by distillation or recrystallization as required.

EXAMPLES

Example 1

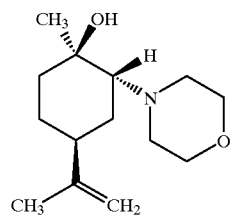

(–)-(1R,2R,4S)-1-Methyl-4-(1-methylethenyl)-2-(4-morpholino)cyclohexanol

A 250-mL, single-neck flask equipped with a magnetic stirring bar and a reflux condenser fitted with a nitrogen bubbler was charged with 54.78 g (0.360 mol) of (S)-(–)-limonene oxide, 90 mL of morpholine, and 10 mL of deionized water. The mixture was heated to reflux and held there for 68.5 h. The reaction mixture was cooled to room temperature. The excess morpholine and limonene oxide were distilled off at reduced pressure to give 64.38 g of crude amino alcohol as a dark orange, viscous oil (PH-9102811-

35). The crude amino alcohol was dissolved in 90 mL of methanol. To the stirred solution, a solution of 33.00 g (0.366 mol) of oxalic acid in 300 mL of methanol was slowly added. A heavy slurry of white solid formed immediately. The slurry was cooled with an ice bath and stirred for 0.5 h. The solid was isolated by filtration, air dried, washed with 75 ml of cold (ice bath) methanol, and vacuum dried at 60° C. to give 54.55 g of the oxalate salt of (−)-(1R,2R,4S)-1-methyl-4-(1-methylethenyl)-2-(4-morpholino)-cyclohexanol as a white solid, mp 206–207° C. (dec). A 1.0 g sample of the oxalate salt was retained for reference. The remainder of the oxalate salt was transferred to a separatory funnel and mixed with 600 mL of 1 N potassium hydroxide and 200 mL of diethyl ether. The mixture was shaken and the layers separated. The aqueous layer was extracted with two 200-mL portions of diethyl ether. The combined ether fractions were washed with 100 mL of deionized water. The ether solution was dried over anhydrous magnesium sulfate. The diethyl ether was removed in vacuo (rotary evaporator) leaving 35.56 g of (−)-(1R,2R,4S)-1-methyl-4-(1-methylethenyl)-2-(4-morpholino)cyclohexanol as a pale yellow oil. The oil was placed in the freezer over night, but crystallization did not occur. A few seed crystals of (−)-(1R,2R,4S)-1-methyl-4-(1-methylethenyl)-2-(4-morpholino)cyclohexano from a previous batch were added, and crystallization began immediately. The oil completely crystallized, and was broken up with a spatula to give a white solid, mp 43–44° C.

Example 2

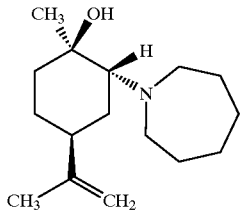

(+)-(1R,2R,4S)-2-(1-Hexamethyleneimino)-1-methyl-4-(1-methylethenyl)cyclohexanol A 250-mL, single-neck flask equipped with a magnetic stirring bar and a reflux condenser fitted with a nitrogen bubbler was charged with 54.78 g (0.360 mol) of (S)-(−)-limonene oxide, 90 mL of hexamethyleneimine, and 10 ml of deionized water. The mixture was heated to reflux and held there for 46 h. The excess hexamethyleneimine and limonene oxide was distilled off at reduced pressure leaving 57.54 g of crude amino alcohol as a dark orange, viscous oil. The crude amino alcohol was dissolved in 75 mL of methanol. To the stirred solution, a solution of 30.00 g (0.333 mol) of oxalic acid in 200 mL of methanol was slowly added. No solid separated. The reaction mixture was allowed to stir at room temperature over night and still no solid separated. The solution was concentrated (rotary evaporator) and allowed to stand in the freezer over night. A white crystalline solid formed. The solid was isolated by filtration, air dried, washed with a small amount of acetone, washed with a small amount of diethyl ether, air dried, and vacuum dried at 60° C. to give 30.66 g of the oxalate salt of (+)-(1R,2R,4S)-2-(1-hexamethyleneimino)-1-methyl-4-(1-methylethenyl)cyclohexanol as an off-white solid, mp 168–171° C. (dec). A 1.00 g sample of the oxalate salt was retained for reference. The remainder was transferred to a separatory funnel and mixed with 400 mL of 1 M potassium hydroxide and 200 mL of diethyl ether. The mixture was shaken and the layers separated. The aqueous layer was extracted with two 200-mL portions of diethyl ether. The combined ether layers were washed with 200 mL of deionized water. The ether solution was dried over anhydrous magnesium sulfate. The ether was removed in vacuo (rotary evaporator) leaving 20.11 g of colorless oil that very rapidly crystallized. The solid was broken up with a spatula to give (+)-(1R,2R,4S)-2-(1-hexamethyleneimino)-1-methyl-4-(1-methylethenyl)cyclohexanol as a white solid, mp 45–47° C.

Example 3

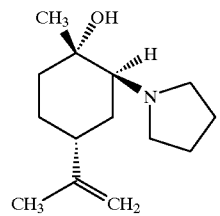

(+)-(1S,2S,4R)-1-Methyl-4-(1-methylethenyl)-2-(1-pyrrolidino)cyclohexanol.

A 250-mL, single-neck flask equipped with a magnetic stirring bar and a reflux condenser fitted with a nitrogen bubbler was charged with 54.78 g (0.360 mol) of (R)-(+)-limonene oxide, 90 mL of pyrrolidine, and 7 mL of deionized water. The mixture was heated to reflux and held there for 45 h. The excess pyrrolidine was distilled off at atmospheric pressure. The residual limonene oxide was distilled off at reduced pressure leaving 60.76 g of crude amino alcohol as a viscous, dark orange oil. The crude amino alcohol was dissolved in 50 mL of methanol. To the stirred solution, a solution of 33.00 g (0.366 mol) of oxalic acid in 100 mL of methanol was added. No solid separated. The solution was cooled with an ice bath and stirred for 1 h. Still no solid separated. The solution was stored in the freezer over night. Still no solid separated. The solution was concentrated (rotary evaporator) and returned to the freezer to stand over night. Still no solid separated. The solvent was removed (rotary evaporator) leaving a thick, viscous, dark oil. The oil was diluted with a small amount of acetone and the resulting solution placed in the freezer. After standing over night, a heavy slurry of crystals had formed. The solid was isolated by filtration, washed with several small portions of acetone, washed with a small portion of diethyl ether, air dried, and vacuum dried at 60° C. to give 28.82 g of the oxalate salt of (+)-(1S,2S,4R)-1-methyl-4-(1-methylethenyl)-2-(1-pyrrolidino)cyclohexanol as a white, crystalline solid, mp 133–135° C. (dec). The crystallization liquors were returned to the freezer and yielded a second crop of crystals. The solid was isolated by filtration, air dried, washed with a small amount of diethyl ether, washed with two small amounts of acetone, washed again with a small amount of diethyl ether, air dried, and vacuum dried at 60° C. to give a 7.91 g second crop of the oxalate salt of (+)-(1S,2S,4R)-1-methyl-4-(1-methylethenyl)-2-(1-pyrrolidino)cyclohexanol as a white, crystalline solid, mp 133–135° C. (dec). A 1.00 g sample of each crop of oxalate salt was taken for reference, and the remainder of both samples were combined and transferred to a separatory funnel. To the funnel were added 400 mL of 1 N potassium hydroxide and 200 mL of diethyl ether. The mixture was shaken and the layers were separated. The aqueous layer was extracted with two 200-mL portions of diethyl ether. The combined ether layers were washed with 200 mL of deionized water. The ether solution was dried over anhydrous magnesium sulfate and the ether was removed in vacuo (rotary evaporator) leaving 23.77 g of pale yellow oil. The oil was stored in the freezer over night and no crystals formed. The oil was warmed to room temperature. A 23.54 g sample of the oil was distilled at reduced pressure to give 23.04 g of (+)-(1S,2S,4R)-1-methyl-4-(1-methylethenyl)-2-(1-pyrrolidino)cyclohexanol as a colorless liquid, bp 128–131° C. (3.0 Torr).

Example 4

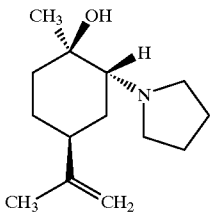

(−)-(1R,2R,4S)-1-Methyl-4-(1-methylethenyl)-2-(1-pyrrolidino)cyclohex-anol

A 250-mL, single-neck flask equipped with a magnetic stirring bar and a reflux condenser fitted with a nitrogen bubbler was charged with 54.78 g (0.036 mol) of (S)-(−)-limonene oxide, 90 mL of pyrrolidine, and 10 mL of deionized water. The mixture was heated to reflux and held there for 44 h. The reflux condenser was replaced with a short path distillation head. The excess pyrrolidine was distilled off at atmospheric pressure. The excess limonene oxide was distilled off at reduced pressure leaving 66.02 g of crude amino alcohol as a pale orange oil. The crude amino alcohol was dissolved in 25 mL of methanol. To that solution, a solution of 33.0 g (0.366 mol) of oxalic acid in 100 mL of methanol was slowly added. The solutions were well mixed, but no solid separated. The flask containing the solution was placed in the freezer. After standing over night in the freezer, only a slight haze of white solid had formed. The solution was concentrated (rotary evaporator). The concentrated solution was diluted with a small amount of acetone and returned to the freezer. After 4–5 h in the freezer, a heavy slurry of white solid had formed. The solid was isolated by filtration, washed with two small portions of acetone, washed with a small amount of diethyl ether, air dried, and vacuum dried at 60° C. to give 18.25 g of the oxalate salt of (−)-(1R,2R,4S)-1-methyl-4-(1-methylethenyl)-2-(1-pyrrolidino)cyclohexanol as a white, crystalline solid, mp 133–135° C. (dec). The crystallization liquor from this material, which also contained the acetone washes, was concentrated (rotary evaporator), diluted with a small amount of acetone, and returned to the freezer. After standing in the freezer over night, a heavy slurry of white solid had formed. The solid was isolated by filtration, washed with two portions of acetone, washed with diethyl ether, air dried, and vacuum dried at 60° C. to give an 11.00 g second crop of the oxalate salt of (−)-(1R,2R,4S)-1-methyl-4-(1-methylethenyl)-2-(1-pyrrolidino)cyclohexanol as a white, crystalline solid, mp 133–135° C. (dec). The crystallization liquors from this material, together with the acetone washes, were returned to the freezer. After standing in the freezer over night, a heavy slurry of white solid formed. The solid was isolated by filtration, washed with two small portions of acetone, air dried, and vacuum dried at 60° C. to give a 13.76 g third crop of the oxalate salt of (−)-(1R,2R,4S)-1-methyl-4-(1-methylethenyl)-2-(1-pyrrolidino)cyclohexanol as a white, crystalline solid, mp 132–134° C. (dec). Retainer samples, 1.00 g each, of each crop of oxalate salt were taken. The remainders of each sample were combined and transferred to a separatory funnel. To the funnel was added 600 mL of 1 N potassium hydroxide and 200 mL of diethyl ether. The mixture was shaken and the layers separated. The aqueous layer was extracted with two 200-mL portions of diethyl ether. The combined ether layers were washed with 200 mL of deionized water. The ether solution was dried over anhydrous magnesium sulfate and the ether was removed in vacuo (rotary evaporator) leaving 27.17 g of crude amino alcohol as a colorless oil. The flask containing the oil was placed in the freezer. After standing in the freezer over night, the oil had not solidified. The oil was warmed to room temperature, and 27.00 g of the oil was transferred to a 50 mL flask and distilled at reduced pressure (short path with a Vigreux column) to give 26.44 g of (−)-(1R,2R,4S)-1-methyl-4-(1-methylethenyl)-2-(1-pyrrolidino)cyclohexanol as a colorless liquid, bp 127–129° C. (2.8 Torr).

Example 5

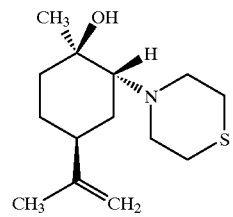

(1R,2R,4S)-1-Methyl4-(1-methylethenyl)-2-(4-thiomorpholino)cyclohexanol

A 250-mL, single-neck flask equipped with a magnetic stirring bar and a reflux condenser fitted with a nitrogen bubbler was charged with 25.00 g (0.242 mol) of thiomorpholine, 76.12 g of (S)-(−)-limonene oxide, and 10 mL of deionized water. The mixture was heated to reflux and held there for 207 h. The progress of the reaction was monitored by capillary GC. The reaction was cooled to room temperature. The excess limonene oxide was distilled off at reduced pressure leaving 55.26 g of crude amino alcohol as a pale orange oil. The crude amino alcohol was dissolved in 50 mL of methanol. To this solution, a solution of 21.81 (0.242 mol) of oxalic acid in 75 mL of methanol was slowly added. A heavy slurry of white solid, which could not be stirred, very quickly formed. The slurry was diluted with an additional 130 mL of methanol and cooled with an ice bath for 0.5 h. The solid was isolated by filtration, washed with 50 mL of cold (ice bath) methanol, washed with a small amount of acetone, air dried, and vacuum dried at 60° C. to give 55.03 g of the oxalate salt of (1R,2R,4S)-1-methyl-4-(1-methylethenyl)-2-(4-thiomorpholino)cyclohexanol as a white solid, mp 197–198° C. (dec). A 1.00 g sample of the oxalate salt was retained for reference. The remainder of the material was transferred to a separatory funnel. To the separatory funnel was added 600 mL of 1 N potassium hydroxide and 200 mL of diethyl ether. The mixture was shaken and the layers separated. The aqueous layer was extracted with two 200-mL portions of diethyl ether. The combined ether layers were washed with 200 mL of deionized water. The ether solution was dried over anhydrous magnesium sulfate and the ether removed in vacuo (rotary evaporator) leaving 36.98 g of amino alcohol as a viscous, pale yellow oil. The oil was placed in the freezer. The oil did not solidify upon standing in the freezer over night. The oil was warmed to room to room temperature and 36.71 g transferred to a 50-mL flask and distilled at reduced pressure (short path with Vigreux column) to give 36.36 g of (1R,2R,4S)-1-methyl-4-(1-methylethenyl)-2-(4-thiomorpholino)cyclohexanol as a highly viscous, colorless oil, bp 163–166° C. (2.5 Torr).

The solvents were removed in vacuo (rotary evaporator) from the crystallization liquor from the oxalate salt leaving a mixture of an orange oil and a white solid. The oil was dissolved approximately 200 mL of acetone to give a slurry of white solid. The solid was isolated by filtration, washed with acetone, air dried, and vacuum dried at 60° C. to give a 5.81 g second crop of the oxalate salt of (1R,2R,4S)-1-methyl-4-(1-methylethenyl)-2-(4-thiomorpholino) cyclohexanol as a white solid, mp 197–198° C. (dec).

Example 6

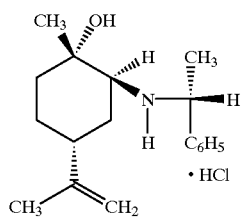

(1S,2S,4R)-1-Methyl-4-(1-methylethenyl)-2-((1R)-1-phenylethylaminno))cyclohexanol Hydrochloride.

A 100-mL, single-neck flask equipped with a magnetic stirring bar and a reflux condenser fitted with a nitrogen bubbler was charged with 15.22 g (0.10 mol) of (R)-(+)-limonene oxide, 7.66 g (0.063 mol) of (R)-(+)-α-methylbenzylamine, and 5 mL of deionized water. The mixture was heated to reflux and held there. After 4 days, and additional 7.61 g (0.05 mol) of (R)-(+)-limonene oxide was added to the reaction mixture, and the reflux was continued. After a total reflux time of 13 days, the reaction mixture was cooled to room temperature. The reaction mixture was transferred to a separatory funnel and diluted with 50 mL of diethyl ether and 50 mL of deionized water. The mixture was made strongly acidic with 12 M hydrochloric acid. The mixture was shaken and the layers were separated. The aqueous layer was extracted with two 50 mL portions of diethyl ether. The ether layers were combined, and a white, crystalline solid formed. The solid was isolated by filtration, washed with diethyl ether, air dried, and vacuum dried at 40° C. to give 11.81 g of the title compound as an off-white, crystalline solid, mp 190–195° C. (dec to dark oil). White crystals had formed in the aqueous layer from the reaction. The crystals were isolated by filtration, washed with diethyl ether, air dried, and vacuum dried at 40° C. to give 1.56 g of the title compound as a white, crystalline solid, mp 214–216° C. (dec).

Example 7

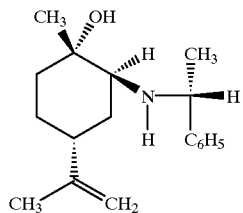

(1S,2S,4R)-1-Methyl-4-(1-methylethenyl)-2-((1R)-1-phenylethylamino))cyclohexanol A 5.50 g sample (1S,2S,4R)-1-methyl4-(1-methylethenyl)-2-((1R)-1-phenylethylamino))cyclohexanol hydrochloride and 75 mL of 1 N potassium hydroxide afforded 4.74 g of (1S,2S,4R)-1-methyl-4-(1-methylethenyl)-2-((1R)-1-phenylethylamino))cyclohexanol as a light orange, thick oil. This material was distilled at reduced pressure (short path with a Vigreux column) to give 4.06 g of (1S,2S,4R)-1-methyl-4-(1-methylethenyl)-2-((1R)-1-phenylethylamino))cyclohexanol as a highly viscous, pale yellow oil, bp 156–160° C. (3.5 Torr). Analysis of this material by capillary GC indicated that it was 98.1 area percent pure.

Example 8

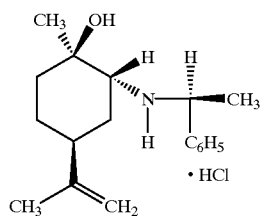

(1R,2R,4S)-1-Methyl-4-(1-methylethenyl)-2-((1S)-1-phenylethylamino))cyclohexanol Hydrochloride A 100-mL, single-neck flask equipped with a magnetic stirring bar and a reflux condenser fitted with a nitrogen bubbler was charged with 36.52 g (0.24 mol) of (s)-(−)-limonene oxide, 12.21 g (0.10 mol) of (S)-(−)-α-methylbenzylamine, and 12 mL of deionized water. The mixture was heated to reflux and held there for 11 days. The reaction mixture was cooled to room temperature. The reaction mixture was transferred to a separatory funnel and diluted with 50 mL of diethyl ether and 50 mL of deionized water. The mixture was made strongly acidic with 12 M hydrochloric acid. The mixture was shaken and the layers were separated. A white solid began to form in the ether layer. The aqueous layer was mixed with 50 mL of diethyl ether and the mixture shaken. White solid formed in both layers. The white solid was isolated from the ether/water mixture and from the ether layer by filtration, washed with diethyl ether, air dried, and vacuum dried at 50–60° C. to give 21.12 g of the title compound as a white, crystalline solid, mp 205–207° C. (dec).

Example 9

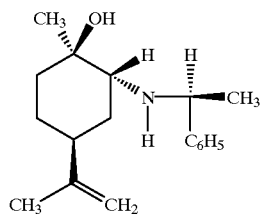

(1R,2R,4S)-1-Methyl-4-(1-methylethenyl)-2-((1S)-1-phenylethylamino))cyclohexanol A 5.50 g sample (1R,2R,4S)-1-methyl-4-(1-methylethenyl)-2-((1S)-1-phenylethylamino))cyclohexanol hydrochloride and 75 mL of 1 N potassium hydroxide afforded 4.48 g of (1R,2R,4S)-1-methyl-4-(1-methylethenyl)-2-((1S)-1-phenylethylamino))cyclohexanol as a yellow, thick oil. This material was distilled at reduced pressure (short path with a Vigreux column) to give 4.00 g of (1R,2R,4S)-1-methyl-4-(1-methyl-ethenyl)-2-((1S)-1-phenylethylamino))cyclohexanol as a highly viscous, pale yellow oil, bp 156–160° C. (3.5 Torr). Analysis of this material by capillary GC indicated that it was 99.2 area percent pure.

Example 10

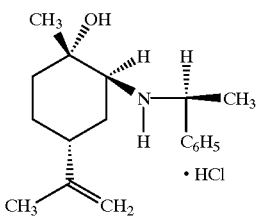

(1S,2S,4R)-1-Methyl-4-(1-methylethenyl)-2-((1S)-1-phenylethylamino))cyclohexanol Hydrochloride A 100-mL, single-neck flask equipped with a magnetic stirring bar and a reflux condenser fitted with a nitrogen bubbler was charged with 38.05 g (0.25 mol) of (R)-(+)-limonene oxide, 12.12 g (0.10 mol) of (S)-(−)-α-methylbenzylamine, and 5 mL of deionized water. The mixture was heated to reflux and held there for 9 days. The reaction mixture was cooled to room temperature. The reaction mixture was transferred to a separatory funnel and diluted with 50 mL of diethyl ether and 50 mL of deionized water. The mixture was made strongly acidic with 12 M hydrochloric acid. The mixture was shaken and the layers were separated. The aqueous layer was extracted with two 50 mL portions of diethyl ether. The ether layers were combined, and upon further dilution with diethyl ether a brown oil separated. The mixture was stirred, and then allowed to stand to permit the oil to separate. The ether was decanted away from the oil. Additional ether was added and the mixture was stirred. The mixture was again allowed to stand to permit the oil to separate. The ether was decanted away from the oil. The oil was dissolved in approximately 300 mL of absolute ethanol. The ethanol was removed in vacuo (rotary evaporator) leaving a solid orange foam. This procedure was repeated two more times leaving a solid orange foam. The orange foam was broken up with a spatula and vacuum dried at 60–70° C. to give 18.11 g of the title compound as a pale orange-brown solid.

Example 11

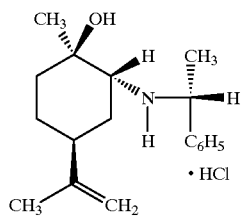

(1R,2R,4S)-1-Methyl-4-(1-methylethenyl)-2-((1R)-1-phenylethylamino))cyclohexanol Hydrochloride A 100-mL, single-neck flask equipped with a magnetic stirring bar and a reflux condenser fitted with a nitrogen bubbler was charged with 38.05 g (0.25 mol) of (S)-(−)-limonene oxide, 12.12 g (0.10 mol) of (R)-(+)-α-methylbenzylamine, and 5 mL of deionized water. The mixture was heated to reflux and held there for 14 days. The reaction mixture was cooled to room temperature. The reaction mixture was transferred to a separatory funnel and diluted with 50 mL of diethyl ether and 50 mL of deionized water. The mixture was made strongly acidic with 12 M hydrochloric acid. The mixture was shaken and the layers were separated. The aqueous layer was extracted with two 50-mL portions of diethyl ether. The ether layers were combined, and upon further dilution with diethyl ether a brown oil separated. The mixture was stirred, and then allowed to stand to permit the oil to separate. The ether was decanted away from the oil. A fresh portion of diethyl ether was added, the mixture shaken, and the oil again allowed to settle out. The mixture was allowed to stand to stand over night. The ether layer was decanted away from the oil. The brown oil was dissolved in 2B absolute ethanol. The ethanol was removed in vacuo (rotary evaporator) leaving a tan crystalline foam. The foam was broken up and dried at 60° C. to give 20.43 g of the title compound as a light tan solid.

Example 12

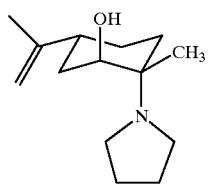

(1S,2S,5R)-2-Methyl-5-(1-methylethenyl)-2-(1-pyrrolidino)cyclohexanol

A 100-mL, single-neck flask equipped with a magnetic stirring bar and a reflux condenser fitted with a nitrogen bubbler was charged with 9.72 g of cis-(R)-(+)-limonene oxide, 50 mL of pyrrolidine, and 5 mL of deionized water. The mixture was heated to reflux and held there for 165 h. The condenser was replaced with a short-path distillation head (equipped with Vigreux column) and the excess pyrrolidine was distilled off at atmospheric pressure leaving the crude product as an orange oil. The crude amino alcohol was transferred to a separatory funnel and mixed with 50 mL of diethyl ether and 50 mL of deionized water. The aqueous layer was made strongly acidic with 12 M hydrochloric acid. The mixture was shaken and the layers were separated. The aqueous layer was extracted with two 50 mL portions of diethyl ether. The aqueous layer was made strongly basic with 50 percent sodium hydroxide and extracted with three 50-mL portions of diethyl ether. The combined ether extracts were washed with 50 mL of deionized water. The ether solution was dried over anhydrous magnesium sulfate and the ether removed in vacuo (rotary evaporator) leaving 10.40 g of amino alcohol as an orange oil. Upon standing over night, the oil crystallized. The oil was recrystallized from hexane to give 1.40 g of fine, white needles. The hexane was removed from the crystallization liquor and the residue recrystallized from n-heptane to give 2.10 g of somewhat thicker white needles. Both of these samples were recrystallized from n-heptane to give 0.67 g of the title compound as white needles, mp 75–76° C., and 1.58 g of white needles, mp 75–76° C., respectively.

Example 13

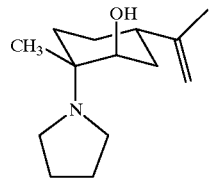

(1R,2R,5S)-2-Methyl-5-(1-methylethenyl)-2-(1-pyrrolidino)cyclohexanol

A 100-mL, single-neck flask equipped with a magnetic stirring bar and a reflux condenser fitted with a nitrogen bubbler was charged with 7.20 g of cis-(S)-(−)-limonene oxide, 50 mL of pyrrolidine, and 2.0 mL of deionized water. The mixture was heated to reflux and held there for 431 h. The condenser was replaced with a short-path distillation head (equipped with a Vigreux column) and the excess pyrrolidine was distilled off at atmospheric pressure. The residue was transferred to a separatory funnel and mixed with 50 mL of diethyl ether and 50 mL of deionized water. The aqueous layer was made strongly acidic with 12 M hydrochloric acid and the mixture shaken. The layers were separated and the aqueous layer was extracted with two 50-mL portions of diethyl ether. The aqueous layer was made strongly basic with 50 percent sodium hydroxide and it was extracted with three 50-mL portions of diethyl ether. The combined ether layers were washed with 50 mL of deionized water. The ether solution was dried over anhydrous magnesium sulfate and the ether was removed in vacuo leaving a pale orange oil that rapidly crystallized. The solid was recrystallized from approximately 30 mL of n-heptane to give 3.74 g of the title compound as white needles, mp 75.5–76.5° C.

Example 14

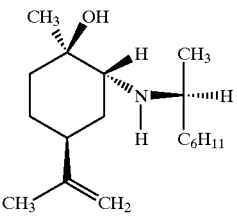

(1R,2R,4S)-2-((1S)-1-Cyclohexylethylamino)-1-methyl-4-(1-methylethenyl)cyclohexanol A 100-mL, single-neck flask equipped with a magnetic stirring bar and a reflux condenser fitted with a nitrogen bubbler was charged with 4.75 g (0.037 mol) of (S)-(−)-1-cyclohexylethylamine, 23.00 g (0.151 mol) of (S)-(−)-limonene oxide, and 2.0 mL of deionized water. The mixture was heated to reflux and held there for 109.75 h. The reaction mixture was cooled to room temperature and filtered to remove an insoluble white solid. The excess limonene oxide was then distilled off at reduced pressure leaving an orange oil that crystallized upon standing over night. The solid was recrystallized from approximately 20 mL of n-heptane to give 3.48 g of (1R,2R,4S)-2-((1S)-1-cyclohexylethylamino)-1-methyl-4-(1-methylethenyl)cyclohexanol, as a white solid, mp 63–64° C.

Example 15

TABLE 1

Preparation of Amino Alcohols from Limonene Oxide and Secondary Amines.

| limonene oxide | amine | amino alcohol | mp/bp(Torr), ° C. | $[\alpha]_D^{23}$ |
|---|---|---|---|---|
| R-(+) | Pyrrolidine | (+)-(1S,2S,4R)-1-methyl-4-(1-methylethenyl)-2-(1-pyrrolidino)cyclohexanol | 128–131 (3.0) | +34.9 (C = 4) (CH$_3$OH) |
| S-(−) | Pyrrolidine | (−)-(1R,2R,4,S)-1-methyl-4-(1-methylethenyl)-2-(1-pyrrolidino)cyclohexanol | 127–129 (2.8) | −34.9 (C = 4) (CH$_3$OH) |
| R-(+) | Piperidine | (+)-(1S,2S,4R)-1-methyl-4-(1-methylethenyl)-2-(1-piperidino)cyclohexanol | >23 133–135 (3.5) | |
| S-(−) | Piperidine | (−)-(1R,2R,4,S)-1-methyl-4-(1-methylethenyl)-2-(1-piperidino)cyclohexanol | >23 135–137 (3.7) | |
| R-(+) | 4-methylpiperidine | (+)-(1S,2S,4R)-1-methyl-4-(1-methylethenyl)-2-(4-methyl-1-piperidino)cyclohexanol | 140–142 (2.5) | |
| S-(−) | 4-methylpiperidine | (−)-(1R,2R,4S)-1-methyl-4-(1-methylethenyl)-2-(4-methyl-1-piperidino)cyclohexanol | 139–142 (3.9) | |
| R-(+) | morpholine | (+)-(1S,2S,4R)-1-methyl-4-(1-methylethenyl)-2-(4-morpholino)cyclohexanol | 43-44 147–150 (3.5) | |
| S-(−) | morpholine | (−)-(1R,2R,4S)-1-methyl-4-(1-methylethenyl)-2-(4-morpholino)cyclohexanol | 41–43 | |
| R-(+) | Thiomorpholine | (+)-(1S,2S,4R)-1-methyl-4-(1-methylethenyl)-2-(4-thiomorpholino)cyclohexanol | 168–171 (4.5) | |
| S-(−) | Thiomorpholine | (−)-(1R,2R,4S)-1-methyl-4-(1-methylethenyl)-2- | 163–166 (2.5) | |

TABLE 1-continued

Preparation of Amino Alcohols from Limonene Oxide and Secondary Amines.

| limonene oxide | amine | amino alcohol | mp/bp(Torr), °C. | $[\alpha]_D^{23}$ |
|---|---|---|---|---|
| R-(+) | Hexamethyleneimine | (+)-(1S,2S,4R)-2-(1-hexamethyleneimino)-1-methyl-4-(1-methylethenyl)cyclohexanol | 148–151 (3.0) | |
| S-(−) | Hexamethyleneimine | (+)-(1R,2R,4S)-2-(1-hexamethyleneimino)-1-methyl-4-(1-methylethenyl)cyclohexanol | 45–47 | +2.4 (C = 4) (CH₃OH) |
| R-(+) | Ethyl 1-piperazinecarboxylate | (+)-(1S,2S,4R)-2-(4-carboethoxy-1-piperazino)-1-methyl-4-(1-methylethenyl)cyclohexanol | 206–209 (3.5) | +6.96 (C = 4) (CH₃OH) |
| R-(+) | Piperazine | (1S,2S,4R)-1-methyl-4-(1-methylethenyl-2-(1-piperazino)-cyclohexanol | 154–157 (3.4) | |
| R-(+) | ethyl isonipecotate | (+)-(1S,2S,4R)-2-(4-carboethoxy-1-piperidino)-2-methyl-4-(1-methylethenyl) cyclohexanol | | +19.2 (C = 4) (CH₃OH) |
| R-(+) | isonipecotic acid | (1S,2S,4R)-2-(4-carboxy-1-piperidino)-2-methyl-4-(1-methylethenyl) cyclohexanol | 141–143 | |
| S-(−) | ethyl isonipecotate | (−)-(1R,2R,4S)-2-(4-carboethoxy-1-piperidino)-2-methyl-4-(1-methylethenyl) cyclohexanol | | −20.1 (C = 4) (CH₃OH) |
| S-(−) | isonipecotic acid | (1R,2R,4S)-2-(4-carboxy-1-piperidino)-2-methyl-4-(1-methylethenyl) cyclohexanol | 121–123 | |
| R-(+) | 1,2,3,4-tetrahydroisoquinoline | (−)-(1S,2S,4R)-1-methyl-4-(1-methylethenyl)-2-(1,2,3,4-tetrahydroisoquinolino) cyclohexanol | 86–88 | −6.3 (C = 4) (CH₃OH) |
| S-(−) | 1,2,3,4-tetrahydroisoquinoline | (+)-(1R,2R,4S)-1-methyl-4-(1-methylethenyl)-2-(1,2,3,4-tetrahydroisoquinolino) cyclohexanol | 86–88 | +6.6 (C = 4) (CH₃OH) |
| R-(+) | 4-benzyl-piperidine | (+)-(1S,2S,4R)-2-(4-benzyl-1-piperidino)-1-methyl-4-(1-methylethenyl) cyclohexanol | 82–84 | +14.5 (C = 4) (CH₃OH) |
| S-(−) | 4-benzyl-piperidine | (31 )-(1R,2R,4S)-2-(4-benzyl-1-piperidino)-1-methyl-4-(1-methylethenyl) cyclohexanol | 77–81 | −14.2 (C = 4) (CH₃OH) |
| R-(+) | imidazole | (+)-(1S,2S,4R)-2-(4-imidazolo)-1-methyl-4-(1-methylethenyl)cyclohexanol | 126–128 | |

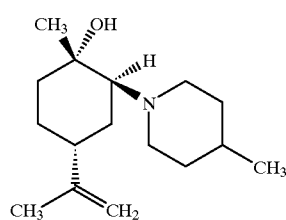

(1S,2S,4R)-1-Methyl-4-(1-methylethenyl)-2-(4-methyl-1-piperidino)cyclohexanol

A 100-ml, single-neck flask equipped with a magnetic stirring bar and a reflux condenser fitted with a nitrogen bubbler was charged with 9.13 g (0.060 mol) of (R)-(+)-limonene oxide, 20 mL of 4-methylpiperidine, and approximately 3 mL of deionized water. The mixture was heated to reflux and held there for 24 h. The reaction mixture was cooled to room temperature. The excess 4-methylpiperidine and limonene oxide were distilled off at reduced pressure leaving 13.38 g of crude amino alcohol as a yellow oil. The oil was dissolved in 15 mL of methanol. To this solution, with stirring, a solution of 4.80 g (0.053 mol) of oxalic acid in 50 mL of methanol was slowly added. No solid separated, even after stirring with ice-bath cooling. The solution was stirred at room temperature with a stream of nitrogen blowing over it. After approximately one-half of the methanol had evaporated, a slurry of white solid formed. The solid was isolated by filtration, washed with 4 mL of cold (ice bath) methanol, air dried, and vacuum dried at 40° C. to give 5.24 g of the oxalate salt of (1S,2S,4R)-1-methyl-4-(1-methylethenyl)-2-(4-methyl-1-piperidino)cyclohexanol as a white solid, mp 168–170° C. (dec). The crystallization liquor yielded a 4.34 g second crop of the oxalate salt of (1S,2S,4R)-1-methyl-4-(1-methylethenyl)-2-(4-methyl-1-piperidino)cyclohexanol as a white solid, mp 175–176° C. (dec). A 1.53 g third crop of the oxalate salt of (1S,2S,4R)-1-methyl-4-(1-methylethenyl)-2-(4-methyl-1-piperidino)-cyclohexanol was also obtained as a white solid. A 3.80 g sample of the second crop oxalate salt was converted to the free base using potassium hydroxide to give 2.58 g of (1S,2S,4R)-1-methyl-4-(1-methylethenyl)-2-(4-methyl-1-piperidino)cyclohexanol as a colorless liquid, bp 140–142° C. (2.5 Torr).

Example 16

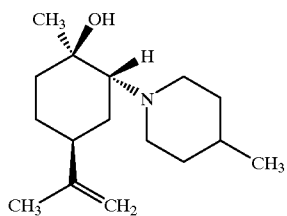

(1R,2R,4S)-1-Methyl-4-(1-methylethenyl)-2-(4-methyl-1-piperidino)cyclohexanol

A 100-mL, single-neck flask equipped with a magnetic stirring bar and a reflux condenser fitted with a nitrogen bubbler was charged with 9.13 g (0.60 mol) of (S)-(−)-limonene oxide, 20 mL of 4-methylpiperidine, and approximately 3 mL of deionized water. The mixture was heated to reflux and held there for 20 h. The excess 4-methylpiperidine and limonene oxide were distilled off under reduced pressure leaving 12.42 g of crude amino alcohol as a pale orange oil. The was dissolved in 15 mL of ethyl acetate. To the stirred solution, a solution of 5.30 g (0.059 mol) of oxalic acid in 50 mL of methanol was slowly added. No crystals formed. The solution was stirred with a stream of nitrogen blowing over it. After some of the solvent had evaporated, a slurry of white solid formed. The solid was isolated by filtration, air dried, washed with 10 mL of cold (ice bath) ethyl acetate, air dried, and vacuum dried at room temperature to give 5.41 g of the oxalate salt of (1R,2R,4S)-1-methyl-4-(1-methylethenyl)-2-(4-methyl-1-piperidino)cyclohexanol as a white, crystalline solid, mp 174–175° C. (dec). A 2.68 g second crop of the oxalate salt was isolated, mp 167–170° C. (dec). A 3.18 g third crop of oxalate salt was isolated, mp 170–172° C. (dec). A 4.59 g sample of the first crop oxalate salt was converted to the free base using potassium hydroxide to give 3.13 g of (1R,2R,4S)-1-methyl-4-(1-methylethenyl)-2-(4-methyl-1-piperidino)cyclohexanol as a colorless liquid, bp 139–142° C.

Example 17

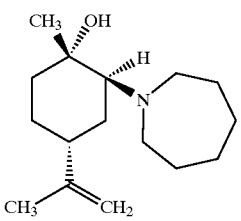

(1S,2S,4R)-1-Methyl-2-(1-hexamethyleneimino)-4-(1-methylethenyl)cyclohexanol

A 100-mL, single-neck flask equipped with a magnetic stirring bar and a reflux condenser fitted with a nitrogen bubbler was charged with 9.13 g (0.060 mol) of (R)-(+)-limonene oxide and 19.10 g of hexamethyleneimine. To this mixture, a few crystals of p-toluenesulfonic acid monohydrate were added and the mixture was heated to reflux and held there for 21.5 h. The reaction mixture was cooled to room temperature. The excess limonene oxide and hexamethyleneimine were distilled off at reduced pressure (2.0 Torr) leaving 13.88 g of crude amino alcohol. This material was distilled at reduced pressure to give 11.10 g of a pale yellow, cloudy liquid, bp 146–149° C. (2.0 Torr) (This was collected as a major fraction, 10.09 g, bp 146–149° C. (2.0 Torr) which was cloudy and pale yellow in color and a minor fraction, 1.01 g, collected mid-stream for NMR analysis, bp 148–149° C. (2.0 Torr) which was a colorless liquid). A solution of 10.00 g of the major fraction in 10 mL of methanol was prepared. To this solution, a solution of 5.50 g (0.061 mol) of oxalic acid in 50 mL of methanol was slowly added. No crystals formed. The solution was stirred at room temperature for 0.5 h, and still no crystals formed. The solution was cooled with an ice bath and stirred for 2 h. No crystals formed. The solution was allowed to stand in a freezer overnight and no crystals formed. The solution was removed from the freezer and stored at room temperature with a small stream of nitrogen blowing over it. After some of the methanol had evaporated crystals began to grow. The crystals were isolated by filtration, washed with ethyl acetate, air dried, and vacuum dried at 40° C. to give 5.95 g of the oxalate salt of (1S,2S,4R)-1-methyl-2-(1-hexamethyleneimino)-4-(1-methylethenyl)cyclohexanol as a white solid, mp 168–171° C. (dec). A 1.78 g second crop of the oxalate salt, mp 168–170° C. (dec) was also obtained. A 4.59 g sample of the first crop oxalate salt was converted to the free base form with potassium hydroxide to give 3.11 g of (1S,2S,4R)-1-methyl-2-(1-hexamethyleneimino)-4-(1-methylethenyl)cyclohexanol as a colorless liquid, bp 148–151° C. (3.0 Torr).

Example 18

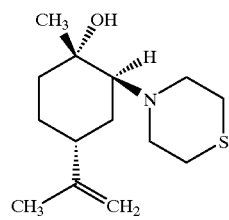

(1S,2S,4R)-1-Methyl-4-(1-methylethenyl)-2-(4-thiomorpholino)cyclohexanol

A 100-mL, single-neck flask equipped with a magnetic stirring bar and a reflux condenser fitted with a nitrogen bubbler was charged with 9.13 g (0.060 mol) of (R)-(+)-limonene oxide, 9.67 g (0.094 mol) of thiomorpholine, and approximately 4 mol of deionized water. The mixture was heated to reflux and held there for 21.5 h. The reaction mixture was cooled to room temperature. The excess limonene oxide and thiomorpholine were distilled off at reduced pressure (2.0 Torr) leaving 9.89 g of amino alcohol as a thick, pale orange oil. The oil was dissolved in 15 mL of methanol. To this solution, a solution of 4.75 g (0.053 mol) of oxalic acid in 45 mL of methanol was slowly added. A very thick slurry of off-white solid formed very quickly. The slurry was diluted with 10 mL of methanol. The solid was isolated by filtration, washed with 25 mL of cold (ice bath) methanol, air dried, and vacuum dried at 40° C. to give 7.82 g of the oxalate salt of (1S,2S,4R)-1-methyl-4-(1-methylethenyl)-2-(4-thiomorpholino)cyclohexanol as an off-white solid, mp 194-195° C. (dec). A 4.59 g sample of the oxalate salt was converted to the free base form with potassium hydroxide to give 3.16 g of (1S,2S,4R)-1-methyl-4-(1-methylethenyl)-2-(4-thiomorpholino)cyclohexanol as a colorless oil. This material was distilled under reduced pressure to give 2.80 g of (1S,2S,4R)-1-methyl-4-(1-methylethenyl)-2-(4-thio-morpholino)cyclohexanol as a colorless, viscous, liquid, bp 168–171° C. (4.5 Torr).

Example 19

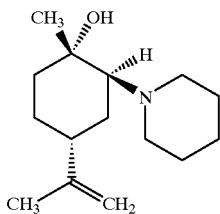

(1S,2S,4R)-1-Methyl-4-(1-methylethenyl)-2-(1-piperidino)cyclohexanol

A 10-mL, single-neck flask equipped with a magnetic stirrer and a reflux condenser was charged with 9.13 g (0.060 mol) of (R)-(+)-limonene oxide, 25 mL of piperidine, and approximately 3 mL of deionized water. The mixture was heated to reflux and held there for 24 h. The excess piperidine and limonene oxide was distilled off at reduced pressure (2.5 Torr) leaving 13.85 g of amino alcohol as a yellow oil. The oil was dissolved in 15 mL of methanol. To this solution, a solution of 5.50 g (0.061 mol) of oxalic acid in 50 mL of methanol was slowly added. A heavy slurry of white crystals quickly formed. The slurry was cooled with an ice bath and stirred for 0.5 h. The solid was isolated by filtration, washed with 15 mL of cold (ice bath) methanol, air dried, and vacuum dried at 40° C. to give 7.48 g of the oxalate salt of (1S,2S,4R)-1-methyl-4-(1-methylethenyl)-2-(1-piperidino)cyclohexanol as a white, crystalline solid, mp 217–218° C. (dec). A 4.59 g sample of the oxalate salt of (1S,2S,4R)-1-methyl-4-(1-methylethenyl)-2-(1-piperidino)cyclohexanol was converted to the free base form with potassium hydroxide to give 3.32 g of (1S,2S,4R)-1-methyl-4-(1-methylethenyl)-2-(1-piperidino)-cyclohexanol as a colorless oil. A 3.11 g sample of this material was distilled at reduced pressure to give 2.86 g of (1S,2S,4R)-1-methyl-4-(1-methylethenyl)-2-(1-piperidino)cyclohexanol as a colorless liquid, bp 133–135° C. (3.5 Torr).

Example 20

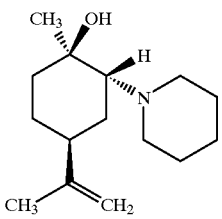

(1R,2R,4S)-1-Methyl-4-(1-methylethenyl)-2-(1-piperidino)cyclohexanol

A 100-mL, single-neck flask equipped with a magnetic stirring bar and a reflux condenser fitted with a nitrogen bubbler was charged with 9.13 g (0.060 mol) of (S)-(–)-limonene oxide, 25 mL of piperidine, and approximately 3 mL of deionized water. The mixture was heated to reflux and held there for 28.75 h. The reaction mixture was cooled to room temperature. The excess piperidine and limonene oxide was distilled off at reduced pressure leaving 12.36 g of amino alcohol as a yellow oil. The oil was dissolved in 15 mL of methanol. To this solution, a solution of 5.50 g of oxalic acid in 50 mL of methanol was slowly added. After approximately on-half of the oxalic acid solution had been added, a slurry of white solid began to form. A heavy slurry of white solid formed upon completion of the addition. The slurry was cooled with an ice bath and stirred for 0.5 h. The solid was isolated by filtration, washed with 15 mL of cold (ice bath) methanol, air dried, and vacuum dried at 40° C. to give 7.90 g of the oxalate salt of (1R,2R,4S)-1-methyl-4-(1-methylethenyl)-2-(1-piperidino)cyclohexanol as a white, crystalline solid, mp 216–217° C. (dec). A 4.59 g sample of the oxalate salt was converted to the free base form with potassium hydroxide to give 3.32 g of (1R,2R,4S)-1-methyl-4-(1-methylethenyl)-2-(1-piperidino)cyclohexanol as a colorless oil. This material was distilled at reduced pressure 2.95 g of (1R,2R,4S)-1-methyl-4-(1-methylethenyl)-2-(1-piperidino)cyclohexanol as a colorless liquid, bp 135–137° C. (3.8 Torr).

Example 21

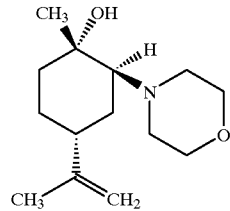

(1S,2S,4R)-1-Methyl-4-(1-methylethenyl)-2-(4-morpholino)cyclohexanol

A 100 mL, single-neck flask equipped with a magnetic stirring bar and a reflux condenser fitted with a nitrogen bubbler was charged with 9.13 g (0.060 mol) of (R)-(+)-limonene oxide, 15 mL of morpholine, and approximately 3 mL of deionized water. The mixture was heated to reflux and held there for 15 h. The reaction mixture was cooled to room temperature. The excess morpholine and limonene oxide were distilled off under reduced pressure (2.0 Torr) leaving 11.69 g of amino alcohol as a pale yellow oil. The oil was dissolved in 10 mL of methanol. To this solution, a solution of 5.50 g (0.061 mol) of oxalic acid in 50 mL of methanol was slowly added. The resulting clear solution was stirred at room temperature and then cooled with an ice bath. After stirring for approximately 10 min, The solution suddenly form a solid mass of white solid. The mass was broken up, stirred, and allowed to warm to room temperature. The solid was isolated by filtration, air dried, washed with 10 mL of cold (ice bath) methanol, air dried, and vacuum dried at 40° C. to give 9.55 g of the oxalate salt of (1S,2S,4R)-1-methyl-4-(1-methylethenyl)-2-(4-morpholino)cyclohexanol as a white, crystalline solid, mp 201–202° C. (dec). A 250 mL separatory funnel was charged with 4.59 g of the oxalate salt of (1S,2S,4R)-1-methyl4-(1-methylethenyl)-2-(4-morpholino)cyclohexanol. To the solid was added 50 mL of 1 N potassium hydroxide. The resulting hazy solution was extracted with three 50 mL portions of hexane. The combined hexane layers were washed with 50 mL of deionized water. The hexane was removed in vacuo (rotary evaporator) leaving 3.28 of (1S,2S,4R)-1-methyl-4-(1-methylethenyl)-2-(4-morpholino)cyclohexanol as a colorless oil. This oil was distilled at reduced pressure to give 3.01 g of (1S,2S,4R)-1-methyl-4-(1-methylethenyl)-2-(4-morpholino)cyclohexanol as a colorless oil, bp 147–150° C. (3.5 Torr).

Example 22

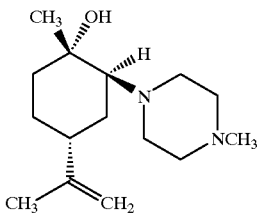

(1S,2S,4R)-1-Methyl-4-(1-methylethenyl)-2-(4-methyl-1-piperazinyl)cyclohexanol

A 250 mL, single-neck flask equipped with a magnetic stirring bar and a reflux condenser fitted with a nitrogen bubbler was charged with 25.04 g (0.250 mol) of 1-methylpiperazine, 76.12 g (0.500 mol) of (R)-(+)-limonene oxide, and 5.0 mL of deionized water. The mixture was heated to reflux and held there for 65 h. The reaction mixture was cooled to room temperature. The excess limonene oxide was distilled off at reduced pressure leaving 65.77 g of crude amino alcohol as an orange oil. The oil was transferred to a 1-L, Erlenmeyer flask equipped with a magnetic stirring bar and was dissolved in 100 mL of acetone. To the acetone solution of the crude amino alcohol, a solution of 22.50 g (0.250 mol) of oxalic acid in 100 mL of acetone was slowly added. A heavy, nearly unstirrable slurry of white solid formed after only a small amount of the oxalic acid solution had been added. Additional acetone was added to the flask until 800 mL of acetone had been added in total. The final slurry was essentially unstirrable. The solid was isolated by filtration, washed with acetone, air dried, and vacuum dried at 60° C. to give 68.80 g of the oxalate salt of (1S,2S,4R)-1-methyl-4-(1-methylethenyl)-2-(4-methyl-1-piperazinyl)cyclohexanol as an off-white solid, mp 160–162□C (dec). A 2.00 g sample of the oxalate salt was retained for reference. The remainder was transferred to a separatory funnel and dissolved in 200 mL of deionized water. He solution was made strongly basic with 50 percent sodium hydroxide (a milky solution formed). The basic solution was extracted with three 150-mL portions of diethyl ether (more water had to be added to the mixture to break up emulsions that formed). The combined ether layers were washed with 200 mL of deionized water. The ether solution was dried over anhydrous magnesium sulfate and the ether was removed in vacuo leaving 42.62 g of (1S,2S,4R)-1-methyl-4-(1-methylethenyl)-2-(4-methyl-1-piperazinyl)cyclohexanol as a yellow oil. The oil was distilled at reduced pressure (short path with a Vigreux column) to give 41.73 g of (1S,2S,4R)-1-methyl-4-(1-methylethenyl)-2-(4-methyl-1-piperazinyl)cyclohexanol as a colorless, viscous liquid, bp 143–147° C. (2.6 Torr).

Example 23

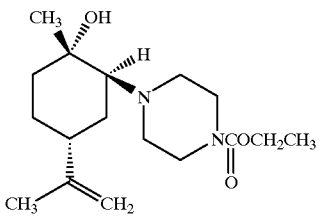

(1S,2S,4R)-2-(4-Carboethoxy-1-piperazinyl)-1-methyl-4-(1-methylethenyl)cyclohexanol A 250 mL, single-neck flask equipped with a magnetic stirring bar and a reflux condenser fitted with a nitrogen bubbler was charged with 39.55 g (0.250 mol) of ethyl 1-piperazinecarboxylate, 76.12 g (0.500 mol) of (R)-(+)-limonene oxide, and 5.0 mL of deionized water. The mixture was heated to reflux and held there for 160 h. The reaction mixture was cooled to room temperature. The excess limonene oxide was distilled off at reduced pressure leaving 71.56 g of crude amino alcohol as a viscous, orange oil. The crude amino alcohol was transferred to a 1-L, Erlenmeyer flask equipped with a magnetic stirring bar and dissolved in 200 mL of acetone. To the solution, a solution of 22.51 g (0.250 mol) of oxalic acid in 150 mL of acetone was slowly added. A heavy slurry of fine, white solid quickly formed. The oxalic acid solution was rinsed into the solution with 50 mL of acetone. The slurry became difficult to stir. The solid was isolated by filtration, washed with acetone, air dried, and vacuum dried at 60° C. to give 75.81 g of the oxalate salt of (1S,2S,4R)-2-(4-(carboethoxy)-1-piperazinyl)-1-methyl-4-(1-methylethenyl)cyclohexanol as an off-white solid, mp 158–160° C. (dec). A 2.00 g sample of the oxalate salt was retained for reference. The remainder was transferred to a separatory funnel and mixed with 600 mL of 1 M potassium hydroxide and 100 mL of diethyl ether. The layers were separated and the aqueous layer was extracted with two 100 mL portions of diethyl ether. The combined ether layers were washed with 100 mL of deionized water. The ether solution was dried over anhydrous magnesium sulfate and the ether was removed in vacuo (rotary evaporator) leaving 50.00 g of (1S,2S,4R)-2-(4-(carboethoxy)-1-piperazinyl)-1-methyl-4-(1-methylethenyl)cyclohexanol as a highly viscous, yellow oil. This material was transferred to a 100-mL single-neck flask and distilled at reduced pressure (short-path with Vigreux column) to give 47.20 g of (1S,2S,4R)-2-(4-(carboethoxy)-1-piperazinyl)-1-methyl-4-(1-methylethenyl)cyclohexanol as a highly viscous, colorless oil, bp 206–209° C. (3.5 Torr).

Example 24

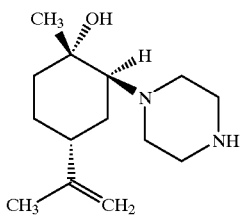

(1S,2S,4R)-1-Methyl-4-(1-methylethenyl)-2-(1-piperazino) cyclohexanol

A 250-mL, three-neck flask equipped with a magnetic stirring bar, a thermometer, a short-path distillation head, and a rubber septum was charged with 30.00 g (0.097 mol) of (1S,2S,4R)-2-(4-carboethoxy-1-piperazino)-1-methyl-4-(1-methylethenyl)-cyclohexanol, 150 mL of n-butanol, and 16.0 g of 50 percent sodium hydroxide. The mixture was heated to reflux, and n-butanol/water distilled off until the temperature in the flask reached 118° C. The distillation head was replaced with a reflux condenser fitted with a nitrogen bubbler and the mixture was held at reflux for 6.5 h. A sample of the reaction mixture was taken and diluted with methanol. Analysis of this sample by capillary GC showed that approximately 3 area percent starting material remained. The reaction mixture was cooled to room temperature and transferred to a separatory funnel. The aqueous layer was extracted with three 100 mL portions of diethyl ether. The combined ether extracts were dried over anhydrous magnesium sulfate. The ether was removed in vacuo (rotary evaporator) leaving the crude amino alcohol as a highly viscous oil. Capillary GC analysis of this material showed that it contained 4 area percent starting material. This material was re-subjected to the hydrolysis conditions and work-up conditions to give 20.76 g of (1S,2S,4R)-1-methyl-4-(1-methylethenyl)-2-(1-piperazino)cyclohexanol as a highly viscous oil. Analysis of this material by capillary GC showed that no starting material was present. This material was distilled at reduced pressure (short-path with Vigreux column) to give 18.15 g of (1S,2S,4R)-1-methyl-4-(1-methylethenyl)-2-(1-piperazino)cyclohexanol as a pale yellow, highly viscous oil, bp 154–157° C. (3.4 Torr).

Example 25

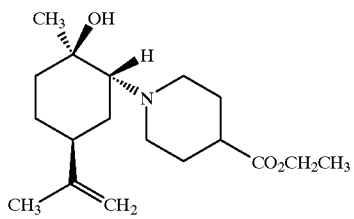

(1R,2R,4S)-2-(4-Carboethoxy-1-piperidino)-1-methyl-4-(1-methylethenyl)cyclohexanol A 3-neck, 250 mL, round-bottom flask with a magnetic stirring bar and a reflux condenser, was charged with 76.21 g of (S)-(−)-Limonene oxide, 39.3 g of ethyl isonipecotate, and 5 mL of deionized water. The mixture was stirred and heated to 100° C. on Station #2 of a six position Electromantle ME heating mantle. The reaction mixture was held at that temperature for 120 h. The reaction mixture was cooled to room temperature. The excess limonene oxide was distilled off at reduced pressure leaving a mixture of an oil and a solid. To the crude amino alcohol/solid mixture, 200 mL of acetone was added, and the slurry stirred with a magnetic stirring bar for 1 h. The pale yellow solid did not dissolve, so it was isolated by filtration (washed with 100 mL. of acetone) and dried at 55° C. in a vacuum oven for approximately 4 hours to yield 13.71 g of a pale yellow solid. (The NMR taken of this material indicated that it was isonipecotic acid). The acetone filtrate was returned to a flask. A solution of 22.51 g (0.25 mol) of oxalic acid in 100 mL. acetone was added slowly to the crude amino alcohol via cannula. A fine white precipitate began to appear. Another 100 mL of acetone was added to improve stirring. The mixture was allowed to stir for 30 min. The product was isolated by filtration (washed with approximately 300 mL. acetone intermittently) and dried under vacuum oven at 55° C. to give 19.35 g of oxalate salt of (1R,2R,4S)-2-(4-carboethoxy-1-piperidino)-1-methyl-4-(1-methylethenyl)cyclohexanol The oxalate salt was transferred to a separatory funnel. To the funnel was added 500 mL of 1N potassium hydroxide and 200 mL of diethyl ether. The mixture was shaken and the layers separated. The aqueous layer was extracted with two 200 mL portions of diethyl ether. The combined ether layers were washed with 200 mL deionized water The ether solution was dried over anhydrous magnesium sulfate and the ether was removed in vacuo (rotary evaporator) leaving 13.3 grams of (1R,2R,4S)-2-(4-carboethoxy-1-piperidino)-1-methyl-4-(1-methylethenyl)cyclohexanol as a clear colorless oil. This material was distilled under reduced pressure to give 11.53 g of (1R,2R,4S)-2-(4-carboethoxy-1-piperidino)-1-methyl-4-(1-methylethenyl)cyclohexanol, bp 183–186° C. (2.5 Torr).

Example 26

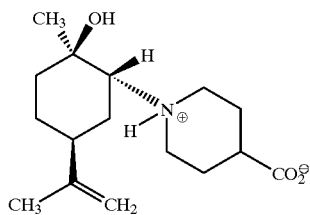

(1R,2R,4S)-2-(4-Carboxy-1-piperidino)-1-methyl-4-(1-methylethenyl)cyclohexanol

A 100-mL, single neck flask equipped with a magnetic stirring bar and a reflux condenser fitted with a nitrogen bubbler was charged with 7.26 g (0.024 mol) of (1R,2R,4S)-2-(4-carboethoxy-1-piperidino)-1-methyl-4-(1-methethenyl)cyclohexanol, 3.50 g (0.028 mol) of 45 percent potassium hydroxide, and 20 mL of isopropanol. The mixture was heated to reflux and held there for 2.5 h. The mixture was cooled to room temperature and 1.71 g (0.029 mol) of glacial acetic acid was added. No solid separated. The reaction mixture was diluted with 20 mL of isopropanol, and the resulting solution was stirred and cooled with an ice bath. A slurry of fine, white solid formed. The slurry was stirred, with ice bath cooling, for 1 h. The solid was isolated by filtration, washed with 8 mL of cold (ice bath) ethanol, air dried, and vacuum dried at 80° C. to give 4.17 g of (1R,2R,4S)-2-(4-carboxy-1-piperidino)-1-methyl-4-(1-methylethenyl)cyclohexanol as a light tan solid, mp 121–123° C.

Example 27

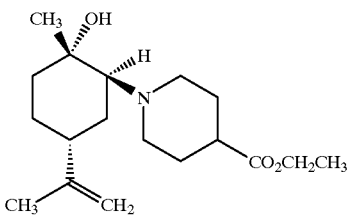

(1S,2S,4R)-2-(4-Carboethoxy-1-piperidino)-1-methyl-4-(1-methylethenyl)cyclohexanol A 3-neck, 250 mL round-bottom flask with a magnetic stirring bar and a reflux condenser was charged with 76.21 g of (R)-(+)-limonene oxide, 39.3 g of ethyl isonipecotate, and 2.5 mL of deionized water. The mixture was stirred and heated to 100° C. on Station #2 of a six position Electromantle ME heating mantle. The mixture was held at that temperature for 10.6 days. The reaction mixture was cooled to room temperature. The excess limonene oxide was distilled off at reduced pressure (60° C. @ 4.0 Torr) leaving a mixture of a pale yellow solid and a brown oil. To the crude amino alcohol product 200 mL of acetone was added, and the mixture was stirred for 1 h. The pale yellow solid (isonipecotic acid) did not dissolve, so it was separated by filtration (washed with 100 mL. of acetone) and dried to yield ~5.0 g. To the acetone filtrate, a solution of 19.64 g (0.218 mol) of oxalic acid in 100 mL of acetone was slowly added via cannula. A fine white precipitate began to appear. Another 100 mL of acetone was added to facilitate stirring. The mixture was allowed to stir for 30 minutes. The product was isolated by filtration, washed with approximately 500 mL acetone intermittently, and vacuum dried at 55° C. overnight to give 52.43 g of oxalate salt of (+)-(1S,2S,4R)-2-(4-carboethoxy-1-piperidino)-1-methyl-4-(1-methylethenyl)cyclohexanol, mp 138–140° C. A 1 gram sample of the oxalate salt was retained. The remaining oxalate salt was transferred to a separatory funnel. To the funnel was added 500 mL of 1N potassium hydroxide and 200 mL. of diethyl ether. The mixture was shaken and the layers were separated. The aqueous layer was extracted with a 200 mL portion of ether. The combined ether layers were washed with 200 mL of deionized water. The ether layer was dried over anhydrous magnesium sulfate, and the ether was removed in vacuo (rotary evaporator) leaving 35.24 g of a clear colorless oil. This material was distilled at reduced pressure (short path with a Vigreux column) to give 32.06 g of (+)-(1S,2S,4R)-2-(4-carboethoxy-1-piperidino)-1-methyl-4-(1-methylethenyl)cyclohexanol as a highly viscous, pale yellow oil, bp 155–160° C. (0.13 Torr).

Example 28

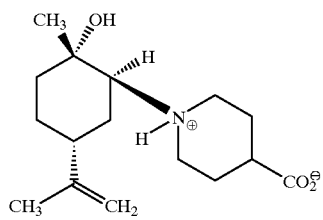

(1S,2S,4R)-2-(4-Carboxy-1-piperidino)-1-methyl-4-(1-methylethenyl)cyclohexanol

A 100-mL, single-neck flask equipped with a magnetic stirring bar and a reflux condenser fitted with a nitrogen bubbler was charged with 15.47 g (0.050 mol) of (1S,2S,4R)-2-(4-carboethoxy-1-piperidino)-1-methyl-4-(1-methylethenyl)cyclohexanol, 7.26 g (0.059 mol) of 45 percent potassium hydroxide, and 20 mL of isopropanol. The mixture was heated to reflux and held there for 3 h. Analysis by capillary GC after 3 h showed that all of the starting ester had been hydrolyzed. The reaction mixture was cooled to room temperature. To the cooled reaction mixture, 3.55 g (0.059 mol) of glacial acetic acid was slowly added. No solid separated. The reaction mixture was diluted with 10 mL of isopropanol and stirred over night at room temperature. A slurry of white solid formed. The slurry was cooled with an ice bath and stirred for 0.5 h. The solid was isolated by filtration, washed with approximately 8 mL of cold (ice bath) isopropanol, air dried, and dried in vacuo at 80° C. to give 9.51 g of (1S,2S,4R)-2-(4-carboxy-1-piperidino)-1-methyl-4-(1-methylethenyl)cyclohexanol as an off-white solid, mp 141–143° C.

Example 29

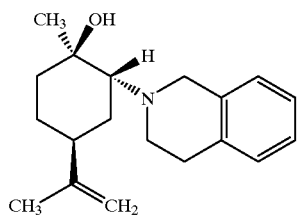

(1R,2R,4S)-1-Methyl-4-(1-methylethenyl)-2-(1,2,3,4-tetrahydroisoquinolino)cyclohexanol A 250 mL, three-neck, round-bottom flask equipped with a magnetic stirring bar and a reflux condenser was charged with 76.21 g of (S)-(–)-limonene oxide, 33.3 g of 1,2,3,4 tetrahydroisoquinoline, and 5 mL. of deionized water. The mixture was heated to 100° C. on Station #3 of a six position Electromantle ME heating mantle and held at that temperature for 10.6 days. The excess limonene oxide was distilled off at reduced pressure (60° C. @ 4 Torr) leaving the crude amino alcohol as a brown solid. The crude amino alcohol was dissolved in 200 mL of acetone, and the solution was stirred for 2 h. To this solution, a solution of 22.51 g (0.25 mol) of oxalic acid in 100 mL of acetone was slowly added via cannula. Immediately a white precipitate formed. After 25 percent of the oxalic acid solution was added, stirring with the magnetic stirring bar became difficult. An additional 200 mL of acetone was added. The oxalic acid solution and acetone were added alternately to keep the slurry stirring. The solid was isolated by filtration, washed with another liter of acetone intermittently, and vacuum dried at 55° C. to give 66.55 g of the oxalate salt of (1R,2R,4S)-1-methyl-4-(1-methylethenyl)-2-(1,2,3,4-tetrahydroisoquinolino) cyclohexanol, mp 147–150° C. A 1 g sample was taken for reference. The remaining oxalate salt was transferred to a separatory funnel. To the funnel were added 500 mL of 1N potassium hydroxide and 200 mL of diethyl ether. The mixture was shaken and the layers separated. The aqueous layer was extracted with two 200 mL of diethyl ether. The combined ether layers were washed with 200 mL deionized water. The ether solution was dried over anhydrous magnesium sulfate, and the ether was removed in vacuo (rotary evaporator) leaving a pale yellow solid. The solid was broken up with a spatula and dried at 35° C. to give 41.72 g of (1R,2R,4S)-1-methyl-4-(1-methylethenyl)-2-(1,2,3,4-tetrahyrdoisoquinolino)cyclohexanol, 78–81° C. This material was recrystallized from approximately 150 mL of n-heptane (with decolorizing carbon) to give, after vacuum drying at 40° C., 27.41 g of (1R,2R,4S)-1-methyl-4-(1-methylethenyl)-2-(1,2,3,4-tetrahyrdoisoquinolino) cyclohexanol as an off-white, crystalline solid, mp 86–88° C.

Example 30

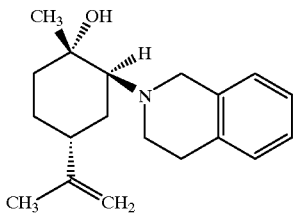

(1S,2S,4R)-1-Methyl-4-(1-methylethenyl)-2-(1,2,3,4-tetrahydroisoquinolino)cyclohexanol A 250 mL, three-neck, round-bottom flask equipped with a magnetic stirring bar and a reflux condenser was charged with 76.21 g of (R)-(+)-limonene oxide, 33.3 g of 1,2,3,4 tetrahydroisoquinoline, and 5 mL. of deionized water. The mixture was heated to 100° C. on Station #3 of a six position Electromantle ME heating mantle and held at that temperature for 10.6 days. The excess limonene oxide was distilled off at reduced pressure (60° C. @ 4 Torr) leaving the crude amino alcohol as a brown solid. The crude amino alcohol was dissolved in 200 mL of acetone, and the resulting solution was stirred for 2 h. To this solution, a solution of 22.51 g (0.25 mol) of oxalic acid in 100 mL of acetone was slowly added via cannula. A white precipitate immediately formed. After 25 percent of the oxalic acid solution had been added, stirring with the magnetic stirring bar became difficult. An additional 200 mL. of acetone was added. The oxalic acid solution and additional acetone were alternately added to allow the mixture to stir. The solid was isolated by filtration, washed with additional liter of acetone intermittently, and vacuum dried at 55° C. to give 56.2 g of the oxalate salt of (1S,2S,4R)-1-methyl-4-(1-methylethenyl)-2-(1,2,3,4-tetrahydroisoquinolino) cyclohexanol, mp 133–136° C. A 1 g sample was taken for reference. The remaining oxalate salt was transferred to a separatory funnel. To the funnel were added 500 mL of 1N potassium hydroxide and 200 mL of diethyl ether. The mixture was shaken and the layers separated. The aqueous layer was extracted with two 200 mL portions of diethyl ether. The combined ether layers were washed with 200 mL of deionized water. The combined ether layers were dried over anhydrous magnesium sulfate, and the ether was removed in vacuo (rotary evaporator) leaving a pale yellow solid. The solid was broken up with a spatula and dried under vacuum at 35° C. to give 33.30 g of (1S,2S,4R)-1-methyl-4-(1-methylethenyl)-2-(1,2,3,4-tetrahydroisoquinolino)cyclohexanol, mp 82–85° C. This material was recrystallized from approximately 150 mL of n-heptane (decolorizing carbon) to give 23.89 g of (1S,2S, 4R)-1-methyl-4-(1-methylethenyl)-2-(1,2,3,4-tetrahydroisoquinolino)cyclohexanol as a white, crystalline solid, 86–88° C.

Example 31

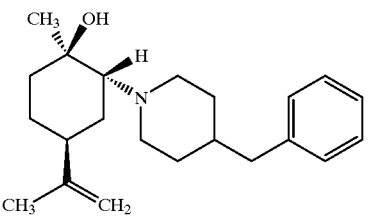

(1R,2R,4S)-2-(4-benzyl-1-piperidino)-1-methyl-4-(1-methylethenyl)cyclohexanol

A 500-mL, three-neck, round-bottom flask equipped with a magnetic stirrer and a reflux condenser fitted with a nitrogen bubbler was charged with 76.0 g of (S)-(−)-limonene oxide, 24.2 g of 4-benzyl-piperidine, and 10 mL of deionized water. The mixture was heated to reflux and held there for 137 h. The excess limonene oxide was distilled off at reduced pressure (60° C. @ 4 Torr) leaving 46.7 g of crude amino alcohol as a light brown solid. The crude amino alcohol was dissolved in 200 mL of acetone. To this solution, solution of 12.43 g (0.138 mol) of oxalic acid in 100 mL of acetone was added slowly via cannula. Immediately upon mixing, a white precipitate formed. An additional 100 mL of acetone was added during the addition of the oxalic acid solution to permit easy stirring of the slurry The solid was isolated by filtration, washed with two 100-mL portions of acetone, air dried, and vacuum dried at 60° C. to give 42.02 g (NOTE: Some of the salt was lost during isolation.) of the oxalate salt of (1R,2R,4S)-2-(4-benzyl-1-piperidino)-1-methyl-4-(1-methylethenyl)cyclohexanol, mp 178–182° C. A 0.80 g sample of the salt was taken for reference. The remainder of the oxalate salt was transferred to a 1-L separatory funnel. To the funnel were added 500 mL of 1N potassium hydroxide and 200 mL of diethyl ether. The mixture was shaken and the layers separated. The aqueous layer was captured in a container. The aqueous layer was extracted with two 200 mL portions of diethyl ether. The combined ether layers were washed with 200 mL deionized water. The ether solution was dried over anhydrous magnesium sulfate. The ether was removed in vacuo (rotary evaporator) leaving a pale yellow solid. The solid was broken up with a spatula to give 29.24 g of (1R,2R,4S)-2-(4-benzyl-1-piperidino)-1-methyl-4-(1-methylethenyl) cyclohexanol, mp 77–81° C.

Example 32

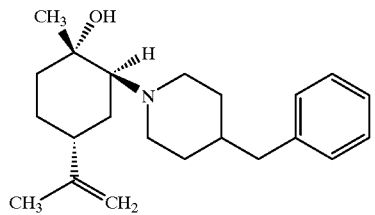

(1S,2S,4R)-2-(4-benzyl-1-piperidino)-1-methyl-4-(1-methylethenyl)cyclohexanol

A three-neck, 250 mL, round-bottom flask equipped with a magnetic stirring bar and a reflux condenser was charged with 76.21 g of (R)-(+)-limonene oxide, 25.00 g of 4-benzylpiperidine and 5 mL of deionized water. The mixture was heated to 100° C. on Station #4 of a six position Electromantle ME heating mantle and held there for 10.6 days. The excess limonene oxide was distilled off at reduced pressure (60° C. @ 4 mmHg) leaving the crude amino alcohol as a light brown solid. The crude amino alcohol was dissolved in 400 mL of acetone. To the acetone solution, a solution of 22.5 g (0.250 mol) of oxalic acid in 100 mL of acetone was slowly added via cannula. Immediately upon mixing, a white precipitate formed. During the addition of the solution of oxalic acid, an additional 300 mL of acetone was added to permit stirring of the slurry. The solid was isolated by filtration, washed with two 100-mL portions of acetone, and vacuum dried at 55° C. to give 40.85 g of the oxalate salt of (1S,2S,4R)-2-(4-benzyl-1-piperidino)-1-methyl-4-(1-methylethenyl)cyclohexanol, mp 175–176° C. A 1.0 g sample of the salt was retained for reference. The remaining oxalate salt was transferred to a 1-L separatory funnel. To the funnel were added 500 mL of 1N potassium hydroxide and 200 mL. of diethyl ether. The mixture was shaken and the layers separated. The aqueous layer was extracted with two 200-mL portions of diethyl ether. The combined ether layers were washed with 200 mL of deionized water. The ether solution was dried over anhydrous magnesium sulfate. The ether was removed in vacuo (rotary evaporator) leaving a pale yellow solid. The solid was broken up with a spatula vacuum dried at 35° C. to give 28.50 g of (1S,2S,4R)-2-(4-benzyl-1-piperidino)-1-methyl-4-(1-methylethenyl)cyclohexanol, mp 76–78° C. This material was recrystallized from n-heptane (decolorizing carbon) to give 17.65 g of (1S,2S,4R)-2-(4-benzyl-1-piperidino)-1-methyl-4-(1-methylethenyl)cyclohexanol, mp 82–84° C.

Example 33

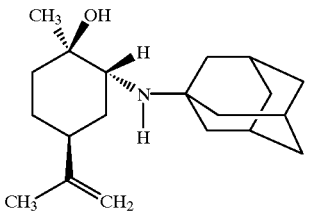

(1R,2R,4S)-2-(1-adamantylamino)-1-methyl-4-(1-methylethenyl)cyclohexanol

A 100-mL, single-neck flask equipped with a magnetic stirring bar and a reflux condenser fitted with a nitrogen bubbler was charged with 7.71 g (0.051 mol) of 1-adamantylamine, 22.83 g (0.150 mol) of (S)-(−)-limonene oxide, and 4.0 mL of deionized water. The mixture was heated to reflux and held there for 31 days. The reaction mixture was filtered to remove some insoluble material. The filter paper was washed with a small amount of n-heptane. Upon cooling, the filtrate solidified to a nearly completely solid mass. The solid was isolated by filtration, washed with a small amount of n-heptane, air dried, and vacuum dried at 40° C. The filtrate was cooled in a freezer to give a second crop of crystals that were isolated and dried in the same manner. The two crops of crystals were combined and recrystallized from 75 mL of n-heptane to give 6.16 g of (1R,2R,4S)-2-(1-adamantylamino)-1-methyl-4-(1-methylethenyl)cyclohexanol as a white solid, mp 94–96° C.

Example 34

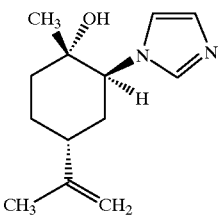

(+)-(1S,2S,4R)-2-(1-Imidazolyl)-1-methyl-4-(1-methylethenyl)cyclohexanol

To (R)-(+)-limonene oxide (6.88 mmol, 1.047 g, 1.13 mL) were added 6 mL of deionized water and imidazole (21 mmol, 1.43 g) at 25° C. A reflux condenser was attached and the flask was set in an oil bath that was heated to 100° C. After 5.0 h at 100° C., the reaction mixture was cooled to 25° C., acidified with 12M hydrochloric acid, and extracted with diethyl ether (7×30 mL). The aqueous layer was cooled to 0° C. and treated with solid sodium hydroxide until the solution was strongly basic to litmus (pH 10). The solution was extracted with methylene chloride (10×30 mL) and the combined extracts were dried. The solvent was removed in vacuo leaving a semi-solid material that was taken up in hot diethyl ether. The solution was cooled to give a white, crystalline solid, mp 126–128° C.; $[\alpha]^{25}_D$=+11.4 (c=3.5 in $CHCl_3$); IR (KBr) 3210.0, 2850.0 $cm^{-1}$.

The NMR spectral data are shown in Table 2.

TABLE 2

NMR Spectral Data for (+)-(1S,2S,4R)-1-methyl-2-(1-imidazolyl)-4-(1-methylethenyl)cyclohexanol in DMSO-$d_6$

| Position | $^{13}C$ (δ ppm) | $^1H$ (δ ppm) |
|---|---|---|
| 1 | 60.8 | 4.10 |
| 2*, 2 | 31.4 | 1.87, 2.08 |
| 3 | 38.2 | 2.40 |
| 4*, 4 | 25.0 | 1.56, 1.80 |
| 5*, 5 | 35.4 | ~1.56 |
| 6 | 70.1 | — |
| 7 | 23.1 | 0.82 |
| 8 | 147.0 | — |
| 9, 9' | 110.3 | 4.80, 4.74 |
| 10 | 20.5 | 1.65 |
| 11 | 119.2 | 7.21 |
| 12 | 127.6 | 6.86 |
| 13 | 137.8 | 7.62 |
| OH | — | 4.70 |

60090

Example 34

TABLE 3

Use of the Limonene Oxide Derived β-Amino Alcohols as Chiral Auxiliaries for the Addition of Diethylzinc to Benzaldehyde

| β-Amino Alcohol | Yield, percent of (R)-1-phenyl-1-propanol | ee, percent | $[\alpha]^{25}D$ |
|---|---|---|---|
| (1S,2S,4R)-1-methyl-4-(1-methylethenyl)-2-(4-morpholino)cyclohexanol | 98 | 78 | 37.5 (c = 1.0 in cyclohexane) |
| (1S,2S,4R)-1-methyl-4-(1-methylethenyl)-2-(1-pyrrolidino)cyclohexanol | 80 | 85 | 43.0 (c = 1.0 in cyclohexane) |
| (1S,2S,4R)-1-methyl-4-(1-methylethenyl)-2-(1-piperidino)cyclohexanol | 80 | 82 | 39.4 (c = 1.0 in cyclohexane) |
| (1S,2S,4R)-2-(benzyl-methylamino)-1-methyl-4-(1-methylethenyl)cyclohexanol | 80 | 85 | 43.0 (c = 1.0 in cyclohexane) |

The following procedure for the synthesis of (R)-1-phenyl-1-propanol is representative: To a 25 mL round bottom flask charged with the β-amino alcohol (1 mmol) was added diethylzinc in toluene (10.0 mL, 10 mmol) under $N_2$. The solution was stirred for 25 min at room temperature and after this was cooled to 0° C. Benzaldehyde (1.0 mL, 10 mmol) was added dropwise via syringe and the reaction was allowed to reach room temperature while stirring overnight. The reaction turned yellow upon adding the benzaldehyde but turned colorless after 24 h of stirring. The reaction was acidified with 12 M hydrochloric acid and extracted with diethyl ether (5×30 mL). The combined organic portions were dried and the solvent was evaporated. The resulting oil was distilled under reduced pressure to obtain the (R)-1-phenyl-1-propanol, bp 47–50° C. (1 Torr).

What is claimed is:

1. A process for preparing a chiral amino alcohol comprising the steps of:

providing an amine starting compound providing a limonene oxide;

refluxing the amine starting compound with the limonene oxide to form a chiral amino alcohol;

removing excess amine and limonene oxide by distilling the chiral amino alcohol at a pressure of less than 10 Torr;

reacting the chiral amino alcohol with oxalic acid in a solvent selected from the group consisting of methanol, acetone and mixtures thereof to form an oxalate salt of the chiral amino alcohol;

neutralizing the oxalate salt with aqueous potassium hydroxide; and purifying the desired amino alcohol by a process selected from distillation and recrystallization.

2. The process of claim 1 wherein the amine starting compound is selected from the group consisting of an alkyl amine with an alkyl group containing four or more carbon atoms, a dialkylamine containing alkyl groups containing four or more carbon atoms and a secondary amine in which the nitrogen is contained in a ring containing four or more carbon atoms.

3. The process of claim 2 wherein the amine starting compound is a secondary amine selected from the group consisting of pyrrolidine, piperidine and hexamethyleneimine.

4. The process of claim 2 wherein the amine starting compound is a secondary amine selected form the group consisting of morpholine, 4-methylpiperazine, 4-ethylpiperazine, ethyl 1-piperazinecarboxylate and thiomorpholine.

5. The process of claim 1 wherein the amine starting compound is selected from the group consisting of (R)-alpha-methylbenzylamine, (S)-alpha-methylbenzylamine, (R)-1-cyclohexylethylamine and (S)-1-cyclohexylethamine.

6. The process of claim 1 wherein the limonene oxide starting compound is selected from the group consisting of (R)-(+)-limonene oxide and (S)-(−)-limonene oxide.

7. A process for preparing a chiral amino alcohol comprising the steps of:

providing an amine starting compound providing a limonene oxide;

refluxing the amine starting compound with the limonene oxide to form a chiral amino alcohol;

cooling the refluxed chiral amino alcohol to room temperature;

dissolving the cooled chiral amino alcohol in diethyl ether;

extracting the cooled chiral amino alcohol into aqueous hydrochloric acid;

extracting the hydrochloric acid solution with diethyl ether to remove any remaining limonene oxide and to form an amine acid salt;

neutralizing the amine acid salt with an aqueous hydrochloride solution selected from the group consisting of sodium hydroxide and potassium hydroxide to a free base form of the amine;

extracting the amino alcohol into diethyl ether;

removing the diethyl ether in vacuo to isolate the amino alcohol; and purifying the desired amino alcohol by a process selected from distillation and recrystallization.

* * * * *